(12) United States Patent
Ortega et al.

(10) Patent No.: US 7,223,079 B2
(45) Date of Patent: May 29, 2007

(54) QUICK LOADING PERISTALTIC PUMP

(75) Inventors: Victor J. Ortega, Kennesaw, GA (US); Pedro Lacasta Egea, Navarra (ES)

(73) Assignee: The Coca-Cola Company, Atlanta, GA (US)

( * ) Notice: Subject to any disclaimer, the term of this patent is extended or adjusted under 35 U.S.C. 154(b) by 547 days.

(21) Appl. No.: 10/628,848

(22) Filed: Jul. 28, 2003

(65) Prior Publication Data

US 2005/0025647 A1   Feb. 3, 2005

(51) Int. Cl.
*F04B 49/06* (2006.01)
*F04B 43/08* (2006.01)

(52) U.S. Cl. .................. 417/53; 417/477.3; 417/477.9

(58) Field of Classification Search ............. 417/477.3, 417/477.8, 477.9, 477.1, 226, 53
See application file for complete search history.

(56) References Cited

U.S. PATENT DOCUMENTS

| | | | |
|---|---|---|---|
| 3,447,478 A | 6/1969 | Clemens | 103/149 |
| 3,963,023 A | 6/1976 | Hankinson | 128/214 |
| 4,178,138 A | 12/1979 | Iles | 417/360 |
| 4,432,707 A | 2/1984 | Anderson et al. | 417/477 |
| 4,549,860 A * | 10/1985 | Yakich | 417/475 |
| 4,558,996 A | 12/1985 | Becker | |
| 4,573,887 A | 3/1986 | Smith | 417/477 |
| 4,832,584 A | 5/1989 | Nassif | 417/477 |
| 5,211,548 A | 5/1993 | Okada | 417/474 |
| 5,318,413 A | 6/1994 | Bertoncini | |
| 5,372,486 A | 12/1994 | Wehling | 417/477.8 |
| 5,388,972 A | 2/1995 | Calhoun et al. | 417/477.11 |
| 5,429,486 A | 7/1995 | Schock et al. | |
| 5,709,539 A | 1/1998 | Hammer et al. | 417/477.3 |
| 5,803,317 A | 9/1998 | Wheeler | 222/214 |
| 5,879,144 A | 3/1999 | Johnson | 417/474 |
| 6,041,709 A * | 3/2000 | Wells et al. | 101/366 |
| 6,419,466 B1 * | 7/2002 | Lowe et al. | 417/477.11 |

FOREIGN PATENT DOCUMENTS

| | | |
|---|---|---|
| DE | 196 47 867 A1 | 5/1998 |
| GB | 851474 | 10/1960 |
| GB | 2 069 063 A | 8/1981 |

* cited by examiner

*Primary Examiner*—Charles G. Freay
(74) *Attorney, Agent, or Firm*—Sutherland Asbill & Brennan LLP

(57) ABSTRACT

A peristaltic pump for transporting a fluid within a flexible tube having a first end, a middle portion, and a second end. The peristaltic pump may include a roller assembly positioned for rotation, a first door positioned adjacent to the roller assembly and pivotable about a first direction, and a second door positioned adjacent to the roller assembly and pivotable about a second direction. The first door and the second door may pivot open and the middle portion of the flexible tube may be positioned about the roller assembly.

23 Claims, 3 Drawing Sheets

QUICK LOADING PERISTALTIC PUMP

TECHNICAL FIELD

The present invention relates generally to a pump and more particularly relates to a peristaltic pump that provides quick and sanitary loading of a fluid tube.

BACKGROUND OF THE INVENTION

Generally described, a peristaltic pump includes a number of pads, drums, or arms rotating within a pair of outer discs. A tube with a fluid to be transported therein generally is positioned adjacent to the drums and a fixed outer surface. As the drums rotate, the fluid within the tube is pushed along and caused to move through the tube. In other words, the fluid is forced along by means of contractions produced mechanically on the flexible tubing.

Peristaltic pumps have been used in the beverage industry with respect to varying types of fluids. One issue associated with a peristaltic pump is the loading and unloading the fluid tube. Loading the tube may be relatively uncomplicated in that the rollers may advance the tube through the overall housing of the pump. Unloading the tube, however, may result in some spillage of the fluid within the housing of the pump. Such spillage may be a concern from an ease of operation point of view and otherwise.

Further, a peristaltic pump generally provides a fixed number of rollers and a fixed pump speed. As such, the pump may not accommodate fluids of varying viscosity or the desire for varying pump speeds. In other words, the pump generally is designed for one specific type of fluid There is a desire therefore, for a peristaltic pump that is easy and clean to use. Such a pump may be quickly and easily modified for varying fluids and speeds.

SUMMARY OF THE INVENTION

The present invention thus provides a peristaltic pump for transporting a fluid within a flexible tube having a first end, a middle portion, and a second end. The peristaltic pump may include a roller assembly positioned for rotation, a first door positioned adjacent to the roller assembly and pivotable about a first direction, and a second door positioned adjacent to the roller assembly and pivotable about a second direction. The first door and the second door may pivot open and the middle portion of the flexible tube may be positioned about the roller assembly.

The peristaltic pump further may include a base such that the roller assembly may be positioned therein and the doors may be pivotably attached thereto. The base may include a tube inlet and a tube outlet positioned thereon. The base also may include an indent for the roller assembly to be positioned therein. The base may include a number of base hinges for pivoting the doors. The doors may include hinges for pivoting about the base.

The first door may include a wall positioned adjacent to the roller assembly so as to define a tube run therein. The second door may include a tube guide positioned thereon. The second door may include an indent for the roller assembly to be positioned therein. The peristaltic pump may include locking mean positioned thereon for the first door and the second door. The base, the first door, and/or the second door may be made out of an acetal resin.

The roller assembly may include a number of rollers mounted on a number of discs. The discs may include a number of roller mounting locations such that the number of rollers may be modified. The roller assembly may include a number of replaceable rollers.

The peristaltic pump further may include a pump motor in communication with the roller assembly. The pump motor may be a variable speed motor.

A further embodiment of the present invention may provide a peristaltic pump system for pumping a predetermined type of fluid within a flexible tube. The system may include a variable speed motor and a roller assembly positioned for rotation in communication with the pump motor. The roller assembly may include a variable number of rollers. The variable speed motor may include about five (5) to about 120 rpm. The variable number of rollers may include about one (1) to about six (6) rollers.

A method of the present invention may provide for pumping a fluid within a flexible tubing with a peristaltic pump. The peristaltic pump may have a pump motor and a roller assembly. The method may include selecting a first predetermined fluid, selecting a first speed for the pump motor based upon the first predetermined type of fluid, selecting a first number of rollers for the roller assembly based upon the first predetermined type of fluid, and pumping the first predetermined type of fluid with the first speed and the first number of rollers.

The method further may include selecting a second predetermined fluid, a second speed for the pump motor, and a second number of rollers and pumping the second predetermined type of fluid with the second speed and second number of rollers.

The first predetermined type of fluid may include coffee, the first speed may include about 30 to 70 rpm, and the first number of rollers may include about three (3) to about four (4) rollers. The first predetermined type of fluid may include orange juice, the first speed may include about 45 to 100 rpm, and the first number of rollers may include about two (2) to about three (3) rollers.

These and other features of the present invention will become apparent upon review of the following detailed description of the preferred embodiments when taken in conjunction with the drawings and the appended claims.

DETAILED DESCRIPTION

Figure 1:
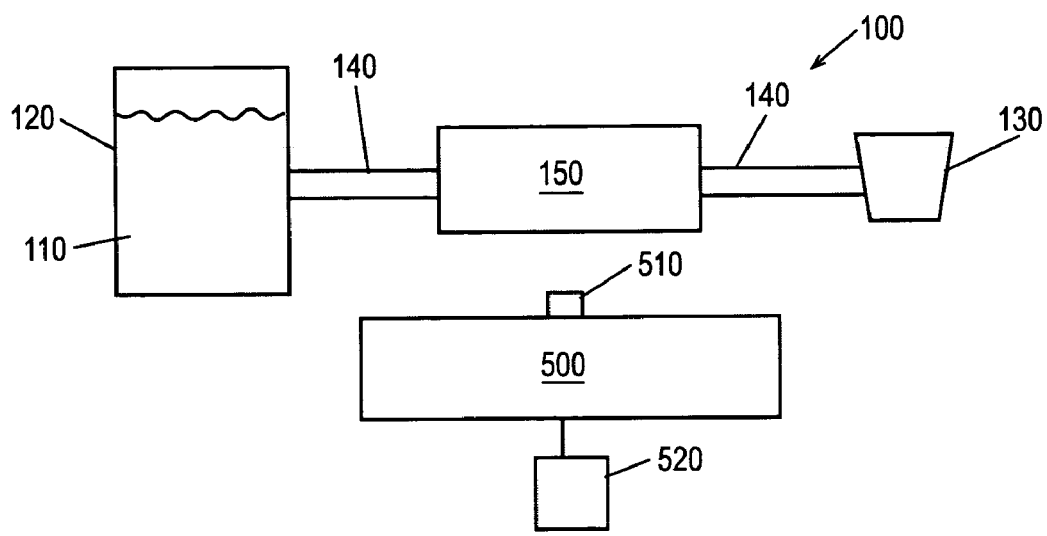
FIG. 1 is a schematic view of a peristaltic pump system of the present invention.
Figure 2:
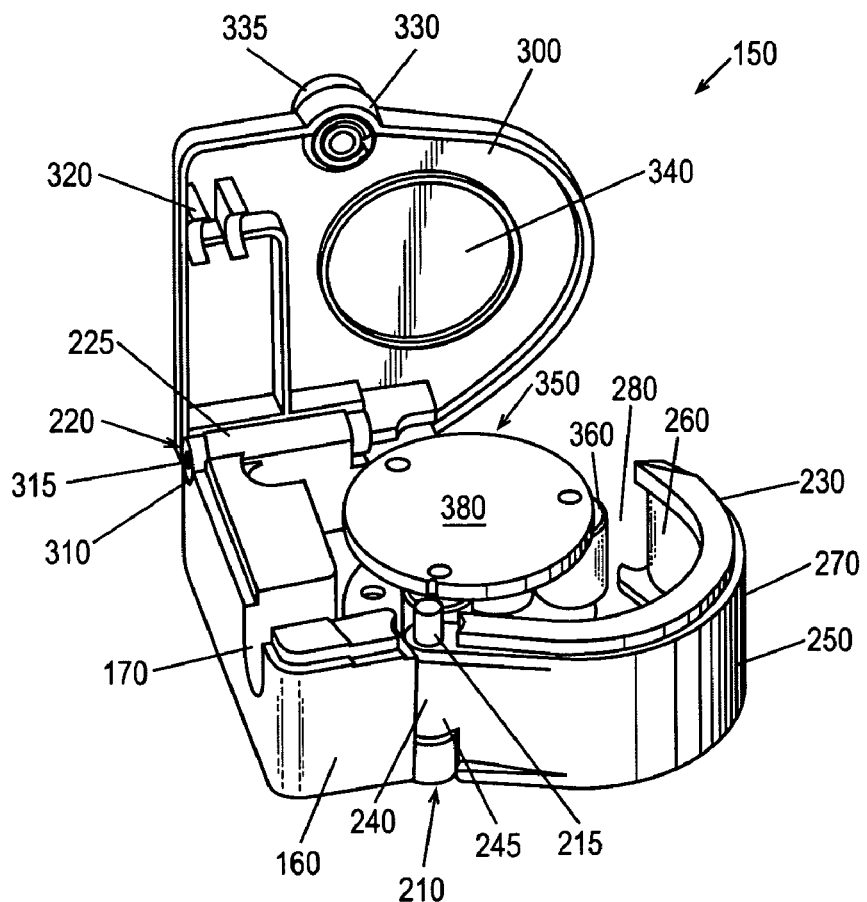
FIG. 2 is a perspective view of a peristaltic pump of the present invention with the door and the lid open.
Figure 3:
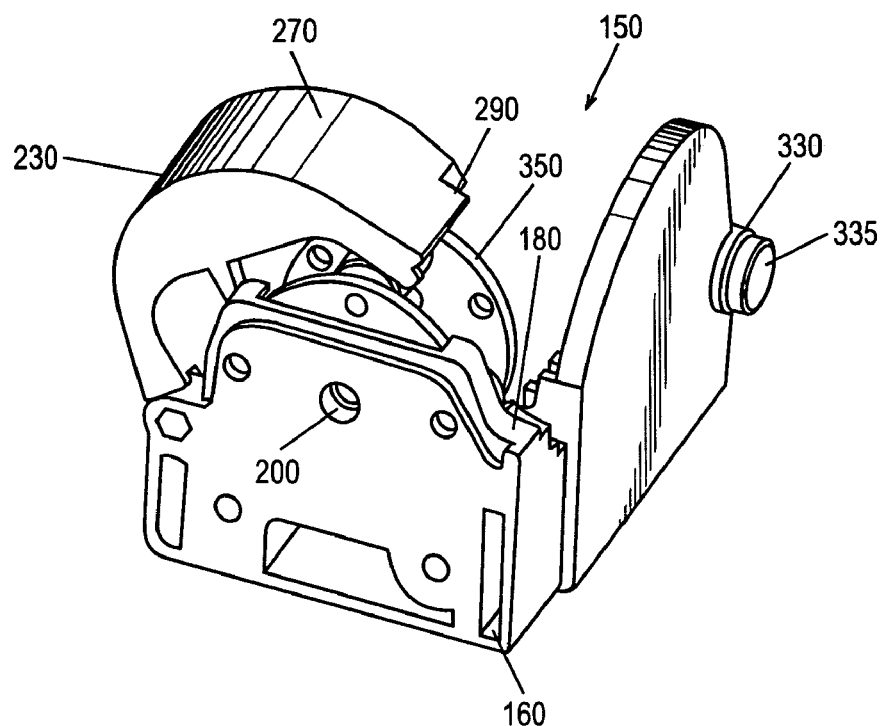
FIG. 3 is a further perspective view of the peristaltic pump of the present invention with the door and the lid open.
Figure 4:
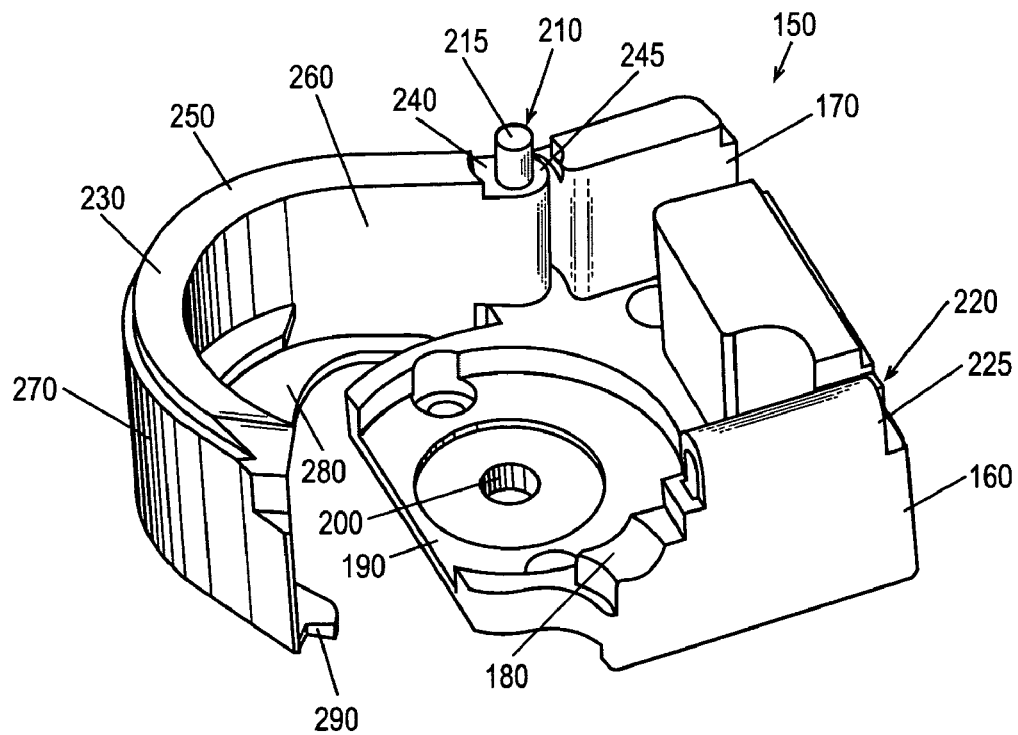
FIG. 4 is a perspective view of the base of the peristaltic pump of FIG. 2 without the roller assembly.

Referring now to the drawings in which like numerals refer to like parts throughout the several views, FIG. 1 shows a schematic view a peristaltic pump system 100 of the present invention. The peristaltic pump system 100 moves a fluid 110. The fluid 110 may be a beverage, a concentrate, an additive, or any other type of liquid. The present invention is not limited by the nature or the flow characteristics of the fluid 110. Specifically, the peristaltic pump system 100 may be used with a fluid or fluids 110 of varying viscosities and/or other types of flow characteristics.

The fluid 110 may be held in a fluid container 120. The fluid container 120 may be any structure designed to hold a fluid 110, including a bag in box or other type of beverage or concentrate container. The peristaltic pump system 100 may transport the fluid 110 from the fluid container 120 to a dispensing area 130. The dispensing area 130 may be a cup or other type of container, a mixing area, or any other type of destination.

The peristaltic pump system 100 may move the fluid 110 from the fluid container 120 to the dispensing area 130 via a length of flexible tubing 140. The flexible tubing 140 may be made out of silicone, silicone composite, or similar types of polymers. The flexible tubing 140 preferably is made out of food grade material. The flexible tubing 140 may have any desired length and/or diameter.

FIGS. 2 through 5 show a peristaltic pump 150 for use with the peristaltic pump system 100. The peristaltic pump 150 may include a base 160. The base 160 may include a tube inlet 170 and a tube outlet 180. The tube inlet 170 and the tube outlet 180 may be formed within the base 160 and may be sized to accommodate the diameter of the flexible tubing 140. The tube inlet 170 and the tube outlet 180 may be spaced apart by about ninety degrees (90°) to about one hundred eighty degrees (180°). Any angle between zero (0°) and one hundred eighty (180°), however, may be used.

The base 160 also may have a roller assembly indent 190. The roller assembly indent 190 may be sized to accommodate a roller assembly as described below. The indent 190 may have the diameter of about 5.3 to about 14 centimeters and may have a depth of about 30 to about 50 millimeters. Any diameter or depth, however, may be used so as to accommodate the shape and size of the roller assembly. The roller assembly indent 190 may have a motor shaft aperture 200 so as to accommodate a motor shaft as described below. The size of the aperture 200 depends upon the size of the motor shaft.

The base 160 further may have a number of hinges, a first hinge 210 and a second hinge 220. The hinges 210, 220 may be made out of shafts and/or cylinders designed to accommodate the shafts. In this embodiment, the first hinge 210 of the base 160 has a shaft 215 extending vertically and the second hinge 220 has a cylinder 225 extending horizontally. Any orientation of shafts and/or cylinders, however, may be used.

The peristaltic pump 150 further may include a door 230. The door 230 may be positioned on and enclose the base 160. The door 230 may have a hinge 240 that accommodates the first hinge 210 of the base 160. As above, the hinge 240 may include a shaft or a cylinder to accommodate a shaft. In this embodiment, the shaft 215 of the first hinge 210 of the base 160 accommodates a cylinder 245 of the door 230.

The door 230 further may include a wall 250. The wall 250 may include a first side 260 and a second side 270. The first side 260 may accommodate a tube run 280. The tube run 280 may be sized to accommodate the flexible tubing 140 between a roller assembly as described below and the position of the first side 260 of the wall 250 so as to provide the pumping action as described below. The wall 250 preferably is substantially semicircular shaped. The door 230 may extend from the hinge 240 about the base 160 to about the tube outlet 180. The door 230 further may have a mating end 290 designed for a snap fit or other type of mating about the tube outlet 180 of the base 160.

The peristaltic pump 150 further may include a lid 300. The lid 300 may be sized to accommodate the size and shape of the base 160. The lid 300 also may have a hinge 310. The hinge 310 may accommodate the second hinge 220 of the base 160. In this embodiment, the hinge 310 may include a shaft 315 to accommodate the cylinder 225 of the second hinge 220. The lid 300 further may include a number of tube guides 320. The tube guides 320 may be sized to accommodate the flexible tubing 140 therein.

The lid 300 further may include a lock aperture 330. The lock aperture 330 may coordinate with the shaft 215 of the first hinge 210 of the base 160. A nut 335 or other type of locking device may be attached to the shaft 215 so as to lock the lid 300 in place.

The lid 300 further may include a roller assembly indent 340 similar to the roller assembly indent 190 described below with respect to the base 160. The roller assembly indent 340 of the lid 300 also may be sized to accommodate the roller assembly as described below.

The components of the peristaltic pump 150 in general, and the base 160, the door 230, and the lid 300 in specific, may be made out of polymers, composites, metals or any other type sufficiently rigid materials. For example, polycarbonate, polyethylene, acrylic or similar types of materials may be used. Further, The base 160, the door 230, and the lid 300 also may be made out of Delrin®, an acetal resin sold by E.I. Dupont de Nemours & Company of Wilmington, Del.

Figure 5:
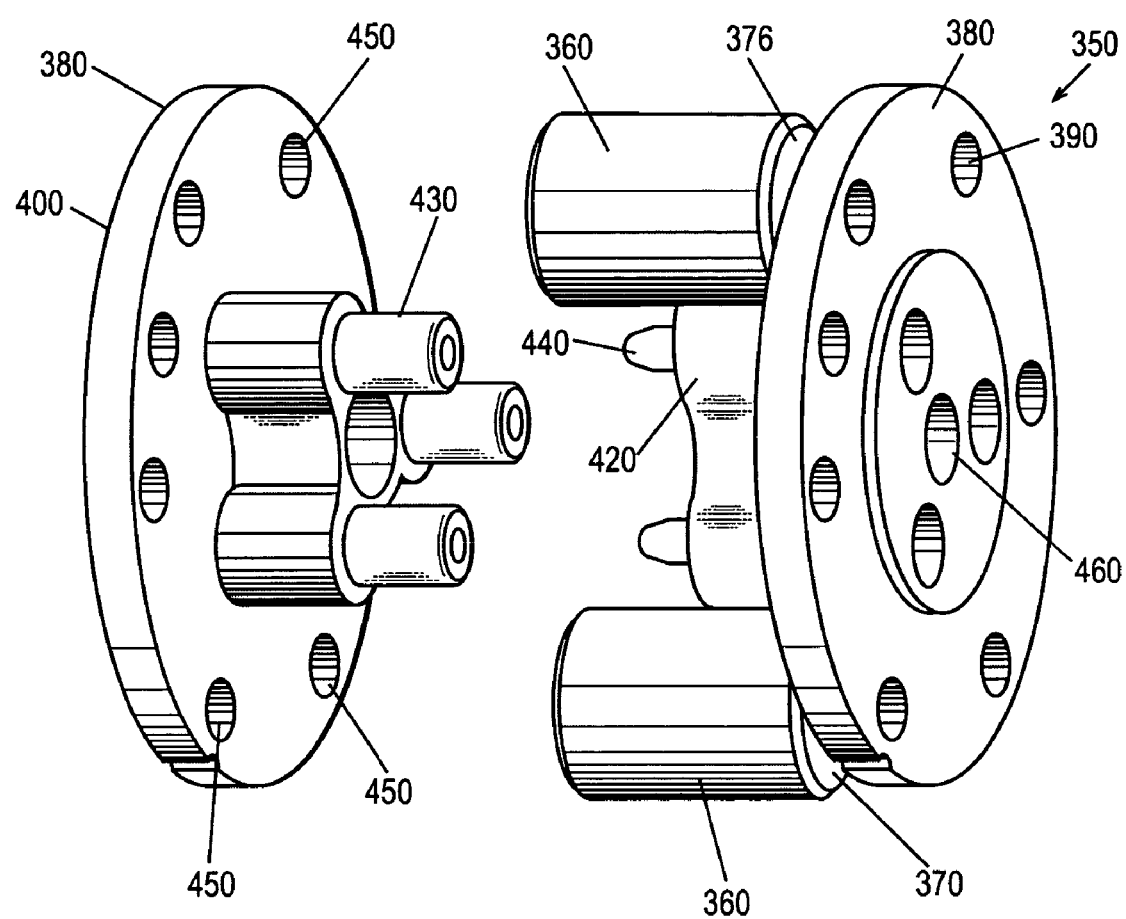
FIG. 5 is an exploded view of the roller assembly of the peristaltic pump of FIG. 2

The peristaltic pump 150 also may include a roller assembly 350 as is shown in, for example, FIG. 5. The roller assembly 350 may include a number of rollers 360. The rollers 360 also may be made out of Delrin® or similar materials. Further, the rollers 360 also may be made out of any material with good wear characteristics such as polycarbonate, Delrin, or similar types of materials. The rollers 360 may have a diameter of about ten (10) to about thirty (30) millimeters and a length of about 28 to 35 centimeters. The rollers 360, however, may have any desired size or shape. The diameter of the rollers 360 may be adjusted to accommodate the diameter of the flexible tube 140. About one (1) to about six (6) rollers 360 generally are used, although any number of rollers 360 may be used. Each roller 360 may have an axle 370 either extending therethrough or molded into each roller 360 and extending out of the lateral ends thereof. The axles 370 may have any convenient size.

The roller assembly 340 also may include a number of outer discs 380. The discs 380 hold both ends of the rollers 360 in place. The discs 380 also may be made out of polycarbonate or any other type of polymer, metal, or other materials with sufficiently rigid characteristics. As is shown, a first disc 390 and a second disc 400 may be used.

The discs 380 may have a number of mating members 410 positioned thereon. In this embodiment, the first disc 390 may have a number of female members 420 while the second disc 400 has a number of male members 430. Further, each of the mating members 410 also may include an internal member 440. The mating members 410 may be arrange in any desired order so as to ensure that the discs 380 stay attached.

The discs 380 also may include a number of roller apertures 450 positioned or formed therein. The roller apertures 450 may be sized so as to accommodate the axles 370 of the rollers 360. Any number of roller apertures 450 may be used so as to vary the number of rollers 360 that the roller assembly 350 as a whole may use. One of the discs 390, 400 also may have drive shaft aperture 460 positioned therein so as to accommodate a drive shaft as described below. In this embodiment, the first disc 390 may have the aperture 460 positioned therein.

The first disc 390 may be positioned within the roller assembly indent 190 of the base 160 while the second disc 400 may be positioned within the roller assembly indent 340 of the lid 300. The roller assembly 350 thus may rotate within the base 160 and the lid 300.

Referring again to FIG. 1, the peristaltic pump system 100 further may include a pump motor 500. The pump motor 500 may be a conventional DC motor or similar type of device. The motor 500 may be about a twenty four (24) volt DC motor. Other voltages also may be used. The pump motor 500 also may be a servomotor, a gear motor with a controller, an AC motor, and similar types of drive devices. The speed of the motor 500 preferably is adjustable. The speed of the pump motor 500 may range from about one (1) rpm to about 140 rpm. The pump motor 500 may include a drive shaft 510 so as to provide rotational force.

Operation of the pump motor 500 and the peristaltic pump system 100 as a whole may be controlled by a control system 520. The control system 520 may vary the speed of the motor 500 and the time of operation. The control system 520 may include a microprocessor or a similar type of control device.

In use, the desired number of rollers 360 may be inserted within the roller assembly 350. The roller assembly 350 is then positioned within the roller assembly indent 190 of the base 160 and mounted on to the drive shaft 510 of the pump motor 500. The controller 520 may be set with a predetermined speed for the pump motor 500.

The flexible tubing 140 may then be inserted within the tube inlet 170 of the base 160. The tubing 140 may then be wrapped around the roller assembly 350 along the tube run 280 and out via the tube outlet 180. The door 230 may then be closed such that the tubing 140 is positioned between the second side 270 of the door 230 and the roller assembly 350. The lid 300 may then be closed and locked. The pump motor 500 then may be activated such that the peristaltic pump system 100 pumps the fluid 510 from the fluid container 120 through the flexible tubing 140 to the dispensing area 130.

Once the fluid container 120 is depleted, the flexible tubing 140 may be removed from the peristaltic pump system 100. Specifically, the lid 300 may be unlocked and opened. The door 230 also may be swung open and the tubing 140 may be removed from the tube outlet 180 and the tube inlet 170. Any open ends of the tubing 140 may be pinched off if needed. Such open ends, however, need not travel through the peristaltic pump system 100. A new tube 140 may then be installed. The tubing 140 thus may be installed and removed without any spillage of the fluid 110.

The number of the rollers 360 and the speed of the pump motor 500 may be varied according to the flow characteristics of the fluid 110 to be used. For example, coffee may have a diluent to concentrate ratio of about 30 to 1 and may use about three (3) to about four (4) rollers 360 with a pump motor 500 speed of about thirty (30) to about seventy (70) rpm, with about 64 rpm preferred. Orange juice concentrate may be more viscous such that a ratio of about 5 to 1 may be used. The pump 150 therefore may use about two (2) to about three (3) rollers 360 and operate at about forty five (45) to about one hundred twenty (120) rpm, with about 82 rpm preferred. Cappuccino concentrate may be more viscous still and have a ratio of about two (2) to about one (1). The pump 150 again may only use about two (2) rollers 360, but run at a higher speed of about 95 rpm. The pump 150 thus can accommodate such varying flow characteristic of the fluid 110.

It should be apparent that the foregoing relates only to the preferred embodiments of the present invention and that numerous changes and modifications may be made herein without departing from the spirit and scope of the invention as defined by the following claims and the equivalents thereof.

We claim:

1. A peristaltic pump for transporting a fluid within a flexible tube having a first end, a middle portion, and a second end, comprising:
    a roller assembly positioned for rotation;
    a first door positioned adjacent to said roller assembly and pivotable about a first direction; and
    a second door positioned adjacent to said roller assembly and pivotable about a second direction;
    wherein said second direction is substantially perpendicular to said first direction; and
    such that said first door and said second door may pivot open and said middle portion of said flexible tube may be positioned about said roller assembly.

2. The peristaltic pump of claim 1, further comprising a base such that said roller assembly may be positioned therein and such that said first door and said second door may be pivotably attached thereto.

3. The peristaltic pump of claim 2, wherein said base comprises a tube inlet and a tube outlet positioned thereon.

4. The peristaltic pump of claim 2, wherein said base comprises an indent for said roller assembly to be positioned therein.

5. The peristaltic pump of claim of claim 2, wherein said base comprises a plurality of base hinges for pivoting said first door and said second door.

6. The peristaltic pump of claim 2, wherein said first door comprises a first door hinge and said second door comprises a second door hinge for pivoting about said base.

7. The peristaltic pump of claim 1, wherein said first door comprises a wall, said wall positioned adjacent to said roller assembly so as to define a tube run therein.

8. The peristaltic pump of claim 1, wherein said second door comprises a tube guide positioned thereon.

9. The peristaltic pump of claim 1, wherein said second door comprises an indent for said roller assembly to be positioned therein.

10. The peristaltic pump of claim 1, further comprising locking means positioned thereon for said first door and said second door.

11. The peristaltic pump of claim 1, wherein said roller assembly comprises a plurality of rollers.

12. The peristaltic pump of claim 11, wherein said roller assembly comprises a plurality of discs so as to mount said plurality of rollers thereon.

13. The peristaltic pump of claim 12, wherein said plurality of discs comprises a plurality of roller mounting locations such that the number of rollers may be modified.

14. The peristaltic pump of claim 1, wherein said roller assembly comprises a plurality of replaceable rollers.

15. The peristaltic pump of claim 1, further comprising a pump motor in communication with said roller assembly.

16. The peristaltic pump of claim 15, wherein said pump motor comprises a variable speed motor.

17. The peristaltic pump of claim 2, wherein said base, said first door, and/or said second door comprise acetal resin.

18. A method of pumping a fluid within a flexible tubing with a peristaltic pump having a pump motor and a roller assembly which can accommodate a variable number of rollers, comprising:
    selecting a first predetermined fluid;
    selecting a first speed for the pump motor based upon the first predetermined type of fluid;

selecting a first number of rollers for the roller assembly based upon the first predetermined type of fluid; and pumping the first predetermined type of fluid with the first speed and the first number of rollers.

19. The method of claim 18, further comprising selecting a second peredetermined fluid, a second speed for the pump motor, and a second number of rollers and pumping the secdond predetermined type of fluid with the second speed and second number of rollers.

20. The peristaltic pump system of claim 18, wherein said variable number of rollers comprises one (1) to six (6) rollers.

21. The method of claim 18, further comprising selecting a second predetermined fluid, a second speed for the pump motor, and a second number of rollers and pumping the second predetermined type of fluid with the second speed and second number of rollers.

22. The method claim 18, wherein the first predetermined type of fluid comprises coffee, the first speed comprises about 30 to about 70 rpm, and the first number of rollers comprises three (3) to four (4) rollers.

23. The method claim 18, wherein the first predetermined type of fluid comprises orange juice, the first speed comprises about 45 to about 100 rpm, and the first number of rollers comprises two (2) to (3) rollers.

* * * * *